Aug. 6, 1968 F. G. CAZZANIGA Plant Pat. 2,827
ROSE PLANT
Filed Feb. 8, 1967
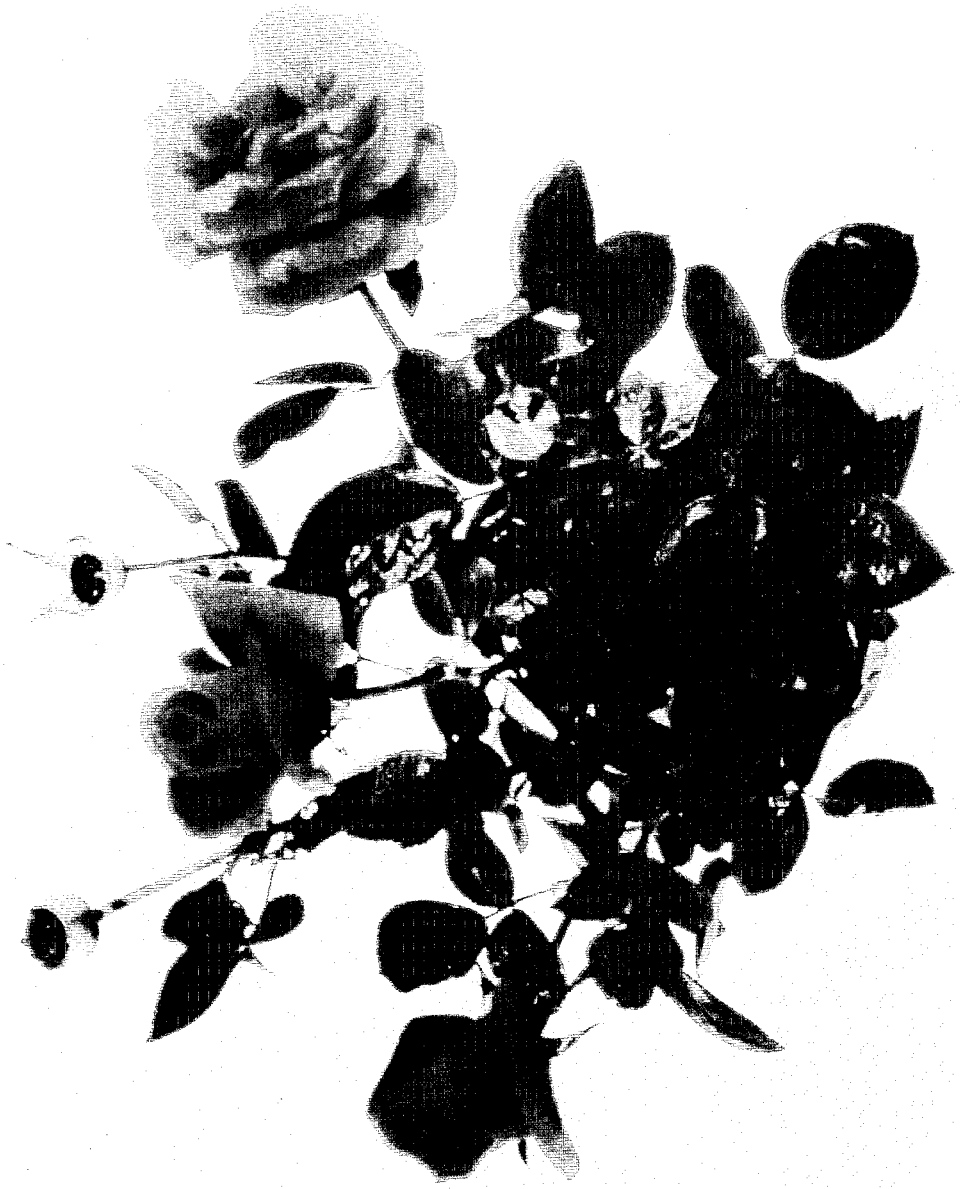
Inventor:
Febo Giuseppe Cazzaniga
By: B. V. Schlesinger
Attorney

United States Patent Office

Plant Pat. 2,827
Patented Aug. 6, 1968

2,827
ROSE PLANT

Febo Giuseppe Cazzaniga, Vimodrone, Milan, Italy, assignor to Fratelli Scarpellini S.p.A., Bergamo, Italy, a company of Italy Filed Feb. 8, 1967, Ser. No. 614,755
Claims priority, application Italy, Feb. 8, 1966, 14,264
1 Claim. (Cl. Pit.—20)

This invention relates to a new and distinct variety of rose plant of the hybrid tea (H. T.) class which was originated by crossing the variety H. T. Inedita F. Cazzaniga with the variety F. (floribunda) Coup de Foudre (not patented). The purpose of this hybridization was to obtain a new variety of rose whose general characteristics would resemble those of H. T. Inedita Cazzaniga, but with more compact and elongated flowers, these being solitary flowers on long, rigid stems suitable for growing for cut flowers, and also abundantly flowering, the shade of color of the flowers differing slightly from H. T. Inedita Cazzaniga.

The aim was entirely satisfactorily attained, the characteristics of the species obtained being clearly distinguishable from those of the parent plants and other species in the same H. T. class; these characteristics may be summarized as follows:

(a) The shape of the flower is more elongated and compact than H. T. Inedita F. Cazzaniga (not patented), with larger, more regular petals;

(b) There is a richer growth of solitary flowers on single stems;

(c) The flowers are of a brighter red on the outside than H. T. Inedita F. Cazzaniga, are attractive, of uniform color, the overall shade corresponding to Vermilion 18 (page 18, H.C.C.).

Asexual reproduction of the new species by gemmae was carried out in Vimodrone, the Province of Milan, Lombardy (Italy), and in the Province of Pistoia in Tuscany. Its characteristics remained unchanged during propagation cycles.

The accompanying drawing shows the variety obtained as regards vegetation and flowering characteristics; the colors shown in this drawing roughly correspond—as far as possible—to the natural colors of the variety under discussion.

Detailed description of the new species: The colors given refer to the Horticultural Color Chart (H.C.C.) and the Color Harmony Manual, fourth edition (C.H.M.).

Parent plants:
Female: H. T. Inedita F. Cazzaniga.
Male: F. Coup de Foudre.

These characteristics were observed at Vimodrone (Milan, Lombardy, Italy) and at Pistoia (Tuscany, Italy) in the open field in the early afternoon about mid-June.

*Flower*

Blooming habit: Recurrent—continuous.

Bud:
*Size.*—Medium.
*Form.*—Elongated oval.
*Color.*—Not affected by changes in atmospheric humidity or heat (when the sepals open): 19 H.C.C.—Scarlet; (when the petals begin to open): inside—18 H.C.C.—Vermilion; outside—19 H.C.C.—Scarlet—(when the petals are half open): inside—18 H.C.C.—Vermilion; outside—19/1 H.C.C.—Scarlet.

Sepals: Tend to grow long and look leafy—they adhere fairly closely to the outside petals—when the flower is open they point straight outwards horizontally.
*Color.*—Inside: 000761/1 H.C.C.—Lavender Green. Outside: green background 061 H.C.C.—Pod Green—mottled with C.H.M. hue 6—ng. 6—Brick Red—Indian Red.
*Calyx.*—Color: 061 H.C.C.—Pod Green. Size: short—narrow. Appearance: smooth.
*Peduncle.*—Length: medium. Appearance: very slight roughness—not completely cylindrical, but slightly flattened on three sides making it roughly triangular in shape. Toughness and bearing: robust and erect. Color: background color 061 H.C.C.—Pod Green—mottled in red C.H.M. hue 6 ng. 6—Brick Red—Indian Red.
*Bud opening.*—Unfolds well. Is not affected by atmospheric humidity or heat.

Bloom:
*Size.*—Medium when fully open, approximately 10–11 cm. Blossoming: several flowers at the same time, each on a solitary long stem—rich growth.
*Stems.*—Long and robust.
*Form.*—Form characteristics of the traditional hybrid tea rose—long-lasting.
*Petalage.*—Double flower—under normal conditions, 30–35 petals. When the flower is open the petals nearest the centre are so arranged as to fill the centre and cover the stamens and pistils.
*Inside of petals.*—18 H.C.C.—Vermilion.
*Outside of petals.*—19/1 H.C.C.—Scarlet.
*Shade of color at a distance.*—18/1 H.C.C.—Vermilion.
*Color.*—Base of petals (aiglet): internally—8 H.C.C.—Cadmium Orange. Outside: 7/2 H.C.C.—Saffron Yellow.
*Discoloration.*—Shade of the whole at the end of the first day: 18/1 H.C.C.—Vermilion. Shade of the whole at the end of the second day: 717/1 H.C.C.—Dutch Vermilion. Shade of the whole at the end of the third day: 717/2 H.C.C.—Dutch Vermilion.

Petals:
*Texture.*—Thick, equal—unchanged by atmospheric humidity and heat.
*Appearance.*—Inside—velvety. Outside—smooth and slightly shiny.
*Form.*—Outside—petals ovoid. Inside—petals tending to a rounded shape.
*Petal arrangement in flower.*—Uniformly imbricate. Central petals—very few—usually large and well-developed.
*Duration of life.*—Last and keep for a long time before fading; then they drop one by one.
*Smell.*—Moderate—delicate smell of apricot—lasts while flower is blowing and a long time after the flowers have been cut.

*Reproductive organs*

Stamens:
*Anthers.*—Average size—evenly spaced around the styles.
*Color.*—7/2 H.C.C.—Saffron Yellow.
*Filaments.*—Medium length color— 21/1 H.C.C.—Carmine.
*Pollen.*—Not observed.

Pistils:
*Styles.*—Bundled together—of almost uniform length—medium length—slender.
*Color.*—21/1 H.C.C.—Carmine.
*Stigmas.*—Color 403/1 H.C.C.—Naples Yellow.
*Ovaries.*—Contained in the calyx.

*Hips.*—None.
*Seeds.*—None.

*Plant*

Form: Shrub.
Growth: Vigorous, upright, branched.
Foliage: Leaves made up of three to five leaflets—very rarely 7.

*Size.*—Average. Terminal leaves are approximately 5 cm. long and 3.5 cm. wide. Basal leaves are 3–5 to 4 cm. long and approximately 2.5 cm. wide.
*Quantity.*—Abundant.
*Color of leaves.*—Right side: 00962 H.C.C.—Parsley Green. Underside: 000761 H.C.C.—Lavender Green.
*Shape.*—Pointed oval.
*Appearance.*—Right side smooth and slightly shiny; underside opaque and glabrous.
*Venation.*—Average relief.
*Margin.*—Mainly toothed, with small single teeth, slightly pointed.
*Petiole.*—Right side color: 000862 H.C.C.—Willow Green. Underside color: 000862/1 H.C.C.—Willow Green. On the underside there are a few small, thin thorns, narrow at the base and slightly curved.
*Stipules.*—Long and adnate to the petiole for four fifths of its length—heads break away outwards—there are very fine teeth on the free margin of the stipules.
*Disease resistance.*—Good resistance to fungus diseases such as black-spot, mildew and rust.

Young wood: Color 000862/1 H.C.C.—Willow Green.
Old Wood: Color 000761/1 H.C.C.—Lavender Green.
*Cortex.*—Smooth.
*Thorns.*—Quantity on large main branches and on branch shoots; abundant and of various sizes. Quantity on branch stems: normal, average amount of thorns. Shape: thin, narrow at the base, protruding horizontally, the tip of the apex slightly curved. Length: medium. Color: young growth—C.H.M. hue 4—pg. 4 (DK Luggage Tan); old growth—C.H.M. hue 4—pg. 4 (Fawn).

What I claim is:

1. A new and distinct variety of rose plant of the hybrid tea class, substantially as herein shown and described, characterized particularly as to novelty by the unique combination of a vigorous and upright habit of plant growth, free blooming habits, suitability for both outdoor and greenhouse culture, elongated oval buds, solitary flowers of traditional form on rigid stems, a distinctive, attractive and uniform color of the flowers, with the inside of the petals of vermilion color and the outside of the petals of scarlet color, the overall shade corresponding to the color vermilion, the flower having a delicate apricot fragrance, good resistance to fungus diseases such as black-spot, mildew and rust, and very long lasting qualities as cut flowers.

No references cited.

ROBERT E. BAGWILL, *Primary Examiner.*